(12) United States Patent
Tsunoda et al.

(10) Patent No.: US 7,915,021 B2
(45) Date of Patent: Mar. 29, 2011

(54) MUTANT FIREFLY LUCIFERASE

(75) Inventors: Hiroyuki Tsunoda, Kodaira (JP); Hideki Kambara, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 226 days.

(21) Appl. No.: 12/222,936

(22) Filed: Aug. 20, 2008

(65) Prior Publication Data
US 2009/0081680 A1    Mar. 26, 2009

(30) Foreign Application Priority Data
Sep. 26, 2007   (JP) ................................ 2007-249669

(51) Int. Cl.
C12N 9/02     (2006.01)
C12Q 1/66     (2006.01)
C12Q 1/26     (2006.01)
C12Q 1/70     (2006.01)
C07H 21/04    (2006.01)

(52) U.S. Cl. .................. 435/189; 435/8; 435/25; 435/6; 536/23.2

(58) Field of Classification Search .................. 435/189, 435/8, 25, 6; 536/23.2
See application file for complete search history.

(56) References Cited

FOREIGN PATENT DOCUMENTS

| JP | 2666561 | 6/1997 |
|---|---|---|
| JP | 09-510610 | 10/1997 |
| JP | 10-512750 | 12/1998 |
| JP | 11-239493 | 9/1999 |
| JP | 3048466 | 3/2000 |
| JP | 2000-197484 | 7/2000 |
| JP | 2000-197487 | 7/2000 |
| JP | 2001-501092 | 1/2001 |
| JP | 2001-518799 | 10/2001 |
| JP | 2003-512071 | 4/2003 |
| JP | 2003-518912 | 6/2003 |
| JP | 2007-094577 | 4/2007 |
| WO | WO 99/02697 | 1/1999 |
| WO | WO 2009/140662 A1 * | 11/2009 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Cont et al., "Crystal Structure of Firefly Luciferase Throws Light on a Superfamily of Adenylate-forming Enzymes", Structure 1996, vol. 4, 287-298.
Nakatsu, et al, "Structural Basis for the Spectral Differenc in Luciferase Bioluminescence", Nature 2006, vol. 440, 372-376.
Cohen et al., "Nonchromosomal Antibiotic Resistance in Bacteria: Genetic Transformation of *Escherichia*", Cohen, S. N. et al.: Proc. Natl. Acad. Sci., USA, 69: 2110-2114 (1972).
Becker, D. M. et al., "High-Efficiency Transformation of Yeast by Electroporation", Methods. Enzymol., 194: 182-187 (1991).
Hinmen, A. et al., "Transformation of Yeast", Proc. Natl. Acad. Sci., USA, 75: 1929-1933 (1978).
Itoh, H., "Transformation of Intact Yeast Cells Treated with Alkali Cations", J. Bacteriol., 153: 163-168 (1983).

* cited by examiner

*Primary Examiner* — Ganapathirama Raghu
(74) *Attorney, Agent, or Firm* — Antonelli, Terry, Stout & Kraus, LLP.

(57) ABSTRACT

This invention relates to: the development of a mutant firefly luciferase in order to use dATP as a DNA polymerase substrate upon pyrosequencing, such luciferase being subjected to substrate specificity modification in a manner such that the dATP-induced activity alone is decreased while the ATP-induced activity is maintained; and a mutant firefly luciferase for which the proportion of activity induced by dATP to activity induced by ATP (dATP/ATP) is lower than that for the wild-type firefly luciferase, in which an amino acid identified based on homology analysis as corresponding with the 421$^{st}$ amino acid (glycine) of the amino acid sequence of the wild-type North American firefly (*Photinus pyralis*) luciferase has been substituted with a polar amino acid.

10 Claims, 3 Drawing Sheets (A)

(B)

MUTANT FIREFLY LUCIFERASE

CLAIM OF PRIORITY

The present application claims priority from Japanese patent application JP 2007-249669 filed on Sep. 26, 2007, the content of which is hereby incorporated by reference into this application.

BACKGROUND OF THE INVENTION

1. Field of the Invention

The present invention relates to a mutant firefly luciferase for which the proportion of activity induced by dATP to activity induced by ATP (dATP/ATP) is lower than such proportion for the wild-type firefly luciferase, the gene thereof, a recombinant vector comprising the gene, and a method for evaluating the activity of the mutant firefly luciferase.

2. Background Art

Sequencing methods based on the Sanger's sequencing method have been widely used as sequencing methods whereby a DNA nucleotide sequence is determined. In such a method, a primer is allowed to bind to a DNA template and a reaction for synthesizing new DNA is carried out by incorporating deoxyribonucleotides (dNTPs: dATP, dGTP, dCTP, and dTTP) with the use of a DNA polymerase, provided that the 3' end of the primer is designated as a starting point. In such case, small amounts of dideoxyribonucleotides (ddNTPs: ddATP, ddGTP, ddCTP, and ddTTP) that have been labeled with four different phosphors are added to a reaction system in a preliminary step. When ddNTPs are incorporated upon reaction, the synthesis reaction is terminated, resulting in generation of DNA fragments in different sizes. Such products contain different phosphors depending on the types of incorporated ddNTP. Thus, the nucleotide sequence of the template DNA can be determined by denaturing such a product into a single strand, followed by electrophoresis and size fractionation.

In the genome project for analyzing the total human DNA nucleotide sequence, sequence analysis was carried out by such a method based on the Sanger's sequencing method. In the project, a sequence analysis apparatus using capillary electrophoresis was newly introduced. Thus, automatic and high-speed analysis has been realized and thus it has become possible to analyze a number of DNA nucleotide sequences.

In recent years, sequence analysis methods based on different principles have been actively developed in order to analyze an increased number of DNA nucleotide sequences at low cost in a rapid manner. For instance, 454 Life Sciences has developed massively parallel high-speed sequencing technology using a system for simultaneously analyzing a number of nucleotide sequences by carrying out a sequence reaction on beads placed on flow cells, and it has already marketed such products.

A method based on principles for sequencing methods used for the massively parallel high-speed sequencing technology is a DNA nucleotide sequence analysis method using bioluminescence, which is also referred to as a pyrosequencing method. In this method, a primer is allowed to bind to a DNA template, 4 types of dNTPs are sequentially added thereto, and then an elongation reaction with the use of a DNA polymerase is carried out. In such case, when a dNTP matched to the template is added, an elongation reaction takes place, resulting in generation of pyrophosphoric acid (PPi). The thus generated PPi is converted into ATP by ATP sulfurylase or the like. Further, the obtained ATP is used as a substrate such that a luciferase induces a luminescent reaction. The occurrence of luminescence indicates incorporation of a matched dNTP, and thus the nucleotide sequence of the template can be determined.

Meanwhile, a luciferase that is used as an enzyme in the above reaction system has a unique characteristic of catalyzing a luminescent reaction. Thus, luciferases are used in a variety of measurement systems involving bacterial count based on ATP quantification, cell proliferation assay, reporter assay for measuring gene transfer activity, intracellular marker/enzyme high sensitive assay, and the like, in addition to sequence analysis. Further, luminescent reactions caused by luciferases can be used at cell, culture tissue, and individual levels. Thus, luciferases are industrially important enzymes that are essential for the field of luminescence imaging.

Thus, in order to achieve further industrial applications of luciferases, a variety of modified luciferases have been developed. For instance, a luciferase having an increased luminescence intensity as a result of substitution in the amino acid sequence has been reported (JP Patent Publication (Kokai) No. 2007-97577 A). It is described that at least one amino acid among the $419^{th}$ to $428^{th}$ amino acids is substituted with a non-polar amino acid (alanine, proline, valine, leucine, isoleucine, methionine, phenylalanine, or tryptophan) having a molecular weight larger than that of the amino acid such that the luminescence intensity is increased.

In addition to the above, the following mutant luciferases have been reported: mutant luciferases having improved thermal stability (JP Patent No. 3048466, JP Patent Publication (Kokai) No. 2000-197487 A, JP Patent Publication (Kohyo) No. 9-510610 A (1997), and JP Patent Publication (Kohyo) No. 2003-518912 A); a mutant luciferase resistant to a surfactant (JP Patent Publication (Kokai) No. 11-239493 A (1999)); mutant luciferases having improved substrate affinity (WO99/02697, JP Patent Publication (Kohyo) No. 10-512750 A (1998), and JP Patent Publication (Kohyo) No. 2001-518799 A); mutant luciferases having different luminescence wavelengths (JP Patent No. 2666561 and JP Patent Publication (Kohyo) No. 2003-512071 A); and a mutant luciferase in which luminescence is maintained at a high level (JP Patent Publication (Kokai) No. 2000-197484 A).

SUMMARY OF THE INVENTION

In connection with sequence analysis using bioluminescence, there is concern that the use of dATP originally used as a substrate for a polymerase is limited. dATP serves as a substrate for luciferase, although its activity is weak. Thus, dATP is undesirably detected via a luminescent signal even when it is not incorporated upon elongation reaction caused by a polymerase. Accordingly, dATP inhibits correct sequence analysis.

In order to solve the above problems, dATPαS, which serves as a substrate for a polymerase but not for a luciferase, is used as an analog instead of dATP (JP Patent No. 3510272). However, compared with the case of dATP, dATPαS is incorporated as a substrate for a polymerase with poor efficiency and thus causes reduction in the reaction efficiency of the overall sequence analysis. Thus, in order to avoid such problem, it is an effective strategy to modify the substrate specificity of luciferase in a manner such that a luciferase does not react with dATP but exclusively reacts with ATP as a substrate.

A luminescent reaction caused by a luciferase has been found to progress in a manner mainly involving two steps. In the first step, a luciferin serving as a luminescent substrate reacts with ATP and thus a luciferyl AMP intermediate is formed, resulting in release of pyrophosphoric acid. In the second step, oxygen reacts with the obtained intermediate. Accordingly, oxyluciferin in an excited state is generated at the same time that AMP and carbon dioxide are generated, resulting in visible radiation emission when the product returns to the ground state.

In general, such luminescent reaction progresses with the use of ATP as a substrate. Since dATP has a structure very similar to that of ATP, dATP is also recognized as a substrate for luciferase, thus allowing a luminescent reaction to progress.

In order to examine the relationship between the structure and the activity of luciferase, some groups have conducted X-ray structural analysis of luciferase proteins. The three-dimensional structure of the North American firefly luciferase (Structure 1996, Vol. 4, 287-298) and the three-dimensional structure of a complex comprising Genji firefly luciferase and a luciferyl AMP intermediate analog have been reported (Nature 2006, Vol. 440, 372-376). The results of three-dimensional structural analysis revealed that a mutation of the $286^{th}$ amino acid (serine) with asparagine directly causes a luminescence color change from yellow-green luminescence to red luminescence (observed in a mutant Genji firefly luciferase).

Based on the judgments regarding data related to the above known three-dimensional luciferase structures, it can be assumed that 2'- and 3'-hydroxyl groups of a sugar portion of ATP serving as a substrate probably form a hydrogen bond with the $422^{nd}$ amino acid (aspartic acid: Asp) of the North American firefly luciferase.

Meanwhile, the structural difference between ATP and dATP merely results from substitution of the 2'-hydroxyl group (2'-OH group) with a hydrogen group (2'-H) in the case of dATP. Thus, it was assumed that the reactivity of luciferase to dATP can be altered by substituting the $422^{nd}$ amino acid (Asp422) with a different amino acid.

Thus, the present inventors produced mutants each obtained by substituting Asp422 with a different amino acid and measured the ATP-induced activities thereof. However, the obtained mutant luciferases were found to completely lack the ATP-induced activity. Therefore, Asp422 was found to be a sequence essential for luciferase activity. Also, it has been found that it is impossible to reduce the activity induced by dATP while maintaining the activity induced by ATP when the amino acid (Asp422) is substituted with a different amino acid.

It is an objective of the present invention to provide a mutant luciferase having a decrease in activity induced by dATP alone while maintaining activity induced by ATP.

In order to solve the above problems, the following strategy was arrived at according to the present invention. The $422^{nd}$ amino acid (aspartic acid: Asp422) is allowed to remain intact and the $421^{st}$ amino acid (glycine: Gly421) adjacent thereto is subjected to amino acid substitution. Then, the structure of a region in the vicinity of Asp422 is deformed such that the activity induced by dATP is reduced.

Since glycine (Gly) has a side chain consisting of hydrogen groups, glycine is an amino acid that has a large degree of structural freedom and thus has much influence on the structure of main chain. Thus, there is a possibility that, when Gly 421 is altered, the structure in the vicinity of a region comprising Asp422 is modified such that the substrate reactivity varies. In view of such possibility, the present inventors modified the nucleotide sequence encoding Gly421 so as to produce mutant luciferases in each of which Gly421 was substituted with any one of 19 different amino acids. Then, the activities with the use of dATP or ATP as a substrate were measured. As a result, the present inventors succeeded in obtaining a mutant luciferase for which the proportion of dATP-induced activity to ATP-induced activity (dATP/ATP) was lower than that for the wild-type luciferase.

The present invention relates to a mutant firefly luciferase for which the proportion of activity induced by dATP to activity induced by ATP (dATP/ATP) is lower than that for the wild-type firefly luciferase, in which an amino acid identified as being located at a position corresponding to the $421^{st}$ amino acid (glycine) of the amino acid sequence of the wild-type North American firefly (*Photinus pyralis*) luciferase has been substituted with a polar amino acid.

In one embodiment of the present invention, examples of a mutant firefly luciferase include a mutant firefly luciferase having an amino acid sequence in which the $421^{st}$ amino acid (glycine) of the amino acid sequence of the wild-type North American firefly (*Photinus pyralis*) luciferase has been substituted with a polar amino acid.

Further, in another embodiment, examples thereof include a mutant firefly luciferase having an amino acid sequence in which the $423^{rd}$ amino acid (glycine) of the amino acid sequence of the wild-type Genji firefly (*Luciola cruciata*) luciferase or the wild-type Heike firefly (*Luciola lateralis*) luciferase has been substituted with a polar amino acid.

In addition, polar amino acids used for substitution are classified into the following two categories (a) and (b).

(a): Group exhibiting "a decrease in the percentage of dATP-induced activity (½ or less) and the maintenance of ATP-induced activity (½ or more):"

Substitution with serine (Ser), lysine (Lys), aspartic acid (Asp), or histidine (His)

(b): Group exhibiting "a decrease in the percentage of dATP-induced activity (⅓ or less) and the maintenance of ATP-induced activity (⅓ or more to less than ½):"

Substitution with arginine (Arg) or asparagine (Asn)

According to the present invention, a gene encoding the mutant firefly luciferase of the present invention and a recombinant vector comprising such gene are also provided.

Further, according to the present invention, a method for evaluating the activity of the mutant firefly luciferase of the present invention is provided. The method comprises the steps of: synthesizing a mutant firefly luciferase for which the proportion of activity induced by dATP to activity induced by ATP (dATP/ATP) is lower than that for the wild-type firefly luciferase; removing endogenous ATP from the synthesized mutant firefly luciferase and purifying the resultant; and measuring the activity induced by ATP and the activity induced by dATP of the purified mutant firefly luciferase.

According to the above method, examples of a mutant firefly luciferase for which the proportion of activity induced by dATP to activity induced by ATP (dATP/ATP) is lower than that for the wild-type firefly luciferase include the above mutant firefly luciferases, which are preferably synthesized in cell-free protein synthesis systems.

EFFECTS OF THE INVENTION

Regarding the mutant firefly luciferase of the present invention, the proportion of dATP-induced activity to ATP-induced activity (dATP/ATP) is lower than that for the wild-type luciferase. Thus, it is possible to use dATP as a DNA polymerase substrate upon pyrosequencing using the mutant firefly luciferase.

DESCRIPTION OF THE PREFERRED EMBODIMENTS

Figure 1:
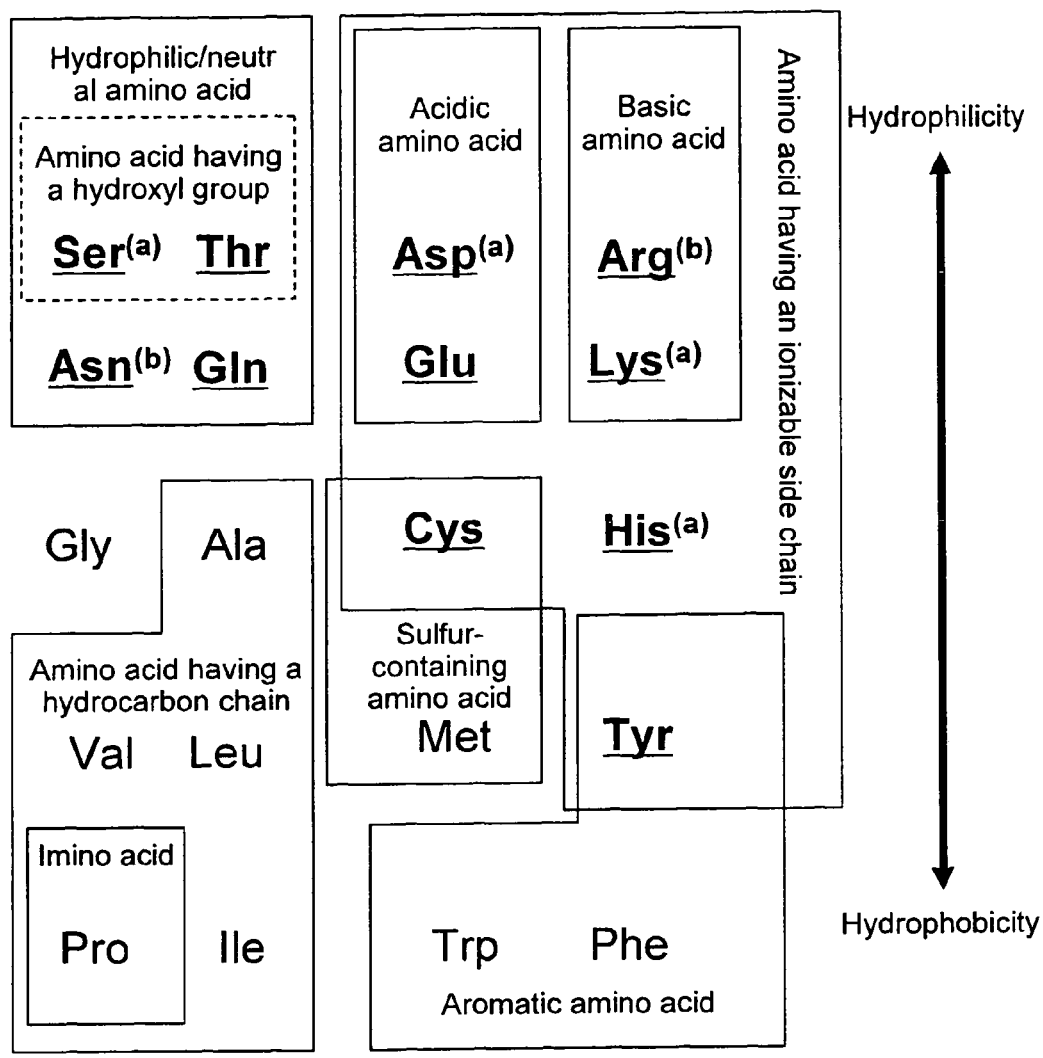
FIG. 1 is a classification chart of amino acids based on their characteristics.

Hereinafter, the present invention is described in detail.

1. Mutant Firefly Luciferase

The mutant firefly luciferase of the present invention is a mutant firefly luciferase that has an amino acid sequence in which an amino acid located at a position corresponding to the $421^{st}$ amino acid (glycine: Gly421) of the amino acid sequence of the wild-type North American firefly luciferase has been substituted with a polar amino acid. For such luciferase, the proportion of dATP-induced activity to ATP-induced activity (dATP/ATP) is lower than that for the wild-type luciferase.

The scientific name of the "North American firefly" according to the present invention is "*Photinus pyralis*." The gene sequence and the amino acid sequence of the wild-type luciferase thereof have been registered as Accession Nos. M15077 (SEQ ID NO: 29; cDNA) and AAA29795 (SEQ ID NO: 30), respectively, in the public database (GenBank).

According to the present invention, "an amino acid located at a position corresponding to the $421^{st}$ amino acid (glycine) of the amino acid sequence of the wild-type North American firefly luciferase" is identified based on homology analysis. At such position, Asp is adjacent to Gly. Thus, as in the case of the North American firefly luciferase, it is considered that substitution of the above Gly with a polar amino acid results in changes in the structure in the vicinity of Asp adjacent to Gly and modifies the substrate reactivity in a manner such that the activity induced by dATP alone is decreased while the activity induced by ATP is maintained. In addition, for homology analysis, any publicly known homology analysis method such as the Limpan-Pearson method can be used.

For instance, in the cases of firefly luciferases derived from the Genji firefly (*Luciola cruciata*) and the Heike firefly (*Luciola lateralis*) (GenBank Accession Nos. M26194 and X66919), the $421^{st}$ amino acid (glycine) of the North American firefly luciferase corresponds to the $423^{rd}$ amino acid (glycine) of the amino acid sequence of each firefly luciferase.

The term "polar amino acid" used in the present invention refers to the following 11 types of amino acids: serine (Ser), threonine (Thr), asparagine (Asn), glutamine (Gln), aspartic acid (Asp), glutamic acid (Glu), arginine (Arg), lysine (Lys), cysteine (Cys), histidine (His), and tyrosine (Tyr).

In the case of a mutant firefly luciferase, the original activity induced by ATP must be maintained even though the activity induced by dATP is decreased. Thus, the balance between the both activity values is important. The above substitution with a polar amino acid is classified into the following two categories (a) and (b) based on a decrease in the percentage of dATP-induced activity and the maintenance of ATP-induced activity.

(a): Group exhibiting "a decrease in the percentage of dATP-induced activity (½ or less) and the maintenance of ATP-induced activity (½ or more):
Substitution with serine (Ser), lysine (Lys), aspartic acid (Asp), or histidine (His)

(b): Group exhibiting "a decrease in the percentage of dATP-induced activity (⅓ or less) and the maintenance of ATP-induced activity (⅓ or more to less than ½):
Substitution with arginine (Arg) or asparagine (Asn)

The term "activity" used herein refers to the maximum value of the luminescence intensity obtained by reacting ATP or dATP with a luciferase in the presence of a magnesium ion and luciferin and measuring the luminescence.

The expression "a decrease in the percentage of dATP-induced activity" means that the value in percentage (%) obtained by measuring the proportion of dATP-induced activity to ATP-induced activity (dATP/ATP) in the case of a mutant luciferase becomes lower than that in the case of the wild-type luciferase.

Thus, the expression "a decrease in the percentage of dATP-induced activity (½ or less)" means that the percentage of dATP-induced activity is decreased to ½ or less for that of the wild-type luciferase. The expression "a decrease in the percentage of dATP-induced activity (⅓ or less)" means that the percentage of dATP-induced activity is decreased to ⅓ or less for that of the wild-type luciferase.

The expression "the maintenance of ATP-induced activity" refers to the level of ATP-induced activity of a mutant luciferase maintained as compared to the wild-type luciferase. Such level is evaluated by synthesizing a mutant luciferase, measuring the ATP-induced activity of the luciferase contained in the crude synthesis solution, and comparing the ATP-induced activity with that in the case of the synthesis of the wild-type luciferase.

Therefore, the expression "the maintenance of ATP-induced activity (½ or more)" means that the ATP-induced activity is maintained at a level equivalent to ½ or more for that of the wild-type luciferase. The expression "the maintenance of ATP-induced activity (⅓ or more to less than ½)" means that the ATP-induced activity is maintained at a level equivalent to ⅓ or more to less than ½ for that of the wild-type luciferase.

The group (a) is a group classified based on "the maintenance of ATP-induced activity" instead of "the percentage of dATP-induced activity." The most preferred example is a mutant (Gly421Ser) in which Gly corresponding to the $421^{st}$ amino acid has been substituted with Ser. The group (b) is a group classified based on "the percentage of dATP-induced activity" instead of "the maintenance of ATP-induced activity." The most preferred example is a mutant (Gly421Asn) in which Gly corresponding to the $421^{st}$ amino acid has been substituted with Asn.

In addition, upon measurement of "the percentage of dATP-induced activity," it is necessary to purify a synthesized luciferase for completely removing components each capable of serving as a substrate of a luciferase, such as endogenous ATP contained in a synthesis reaction solution.

Meanwhile, upon determination of "the maintenance of ATP-induced activity," a portion of a crude synthesis solution (approximately 5 μL) is used before it is subjected to luciferase purification. In such case, the ATP-induced activity is represented by a value indicating two factors, which are the activity of a synthesized luciferase and the tendency to be synthesized (synthesis capacity), instead of an activity value corrected with the value based on the amount of synthesized luciferase. In general, when a protein comprising a mutated amino acid is synthesized, the amount of synthesized protein varies as compared with that of the wild-type protein. In many cases, a mutant protein experiences decreases in thermal stability and folding efficiency, and thus the amount of the synthesized protein decreases. In a case in which a mutant protein is obtained for recombinant production in the future, a mutant protein exhibiting a slight decrease in the level of synthesis capacity is desirable. That is, the above ATP-induced activity measurement method is appropriate for evaluation of a luciferase exhibiting low thermal stability and poor folding efficiency.

Amino acid substitution according to the present invention is summarized in FIG. 1. The aforementioned polar amino acids are underlined in the figure. The amino acids belonging to the group (a) are shown with a superscript notation of (a). The amino acids belonging to the group (b) are shown with a superscript notation of (b).

2. Mutant Firefly Luciferase Gene

According to the present invention, a gene encoding the mutant firefly luciferase of the present invention is provided. In the nucleotide sequence of the gene, the nucleotide sequence encoding an amino acid corresponding to the $421^{st}$ amino acid (Gly) of a mutant North American firefly luciferase has been substituted with a nucleotide sequence encoding a polar amino acid. For instance, in the cases of the Genji firefly and the Heike firefly, a nucleotide sequence encoding an amino acid sequence in which the $423^{rd}$ amino acid (Gly) has been substituted with a polar amino acid is obtained.

Nucleotide sequence substitution can be carried out via site-specific mutation of the wild-type luciferase gene. Any known site-specific mutation method can be used. Such mutation can be carried out using a commercially available kit such as a GeneTailor Site-Directed Mutagenesis System (Invitrogen).

3. Mutant Firefly Luciferase Recombinant DNA Vector

According to the present invention, a recombinant vector obtained by inserting the above mutant firefly luciferase gene into vector DNA is also provided.

Examples of relevant plasmid DNAs include *Escherichia coli*-derived plasmids (e.g. pBR322, pBR325, pUC18, and pUC119), *Bacillus subtilis*-derived plasmids (e.g., pUB110 and pTP5), and yeast-derived plasmids (e.g. YEp13, YEp24, YCp50, and pYE52). Examples of phage DNAs include the M13 phage and λ phage.

A method for inserting the gene of the present invention into the above vector that can be used is a method comprising cleaving purified DNA with an appropriate restriction enzyme, inserting the resultant into an appropriate restriction enzyme site or multi-cloning site of vector DNA, and causing ligation to the vector.

In order to induce the expression of a foreign gene in a host, it is necessary to position an appropriate promoter before a structural gene. Such promoter is not particularly limited. Any promoter known to function in a host can be used. In addition, promoters are described below with the relevant hosts in connection with the transformants described below. Also, if necessary, a cis element such as an enhancer, a splicing signal, a polyA addition signal, a ribosome binding sequence (SD sequence), a terminator sequence, and the like can be positioned. Further, a commercially available expression vector system such as a pET vector system (Novagen) or a pURE vector system (Post Genome Institute Co., Ltd.) can be used.

4. Synthesis of a Mutant Firefly Luciferase

Next, a mutant firefly luciferase protein expression system is prepared by introducing the aforementioned vector into a host in a manner such that a gene of interest can be expressed therein. A host used herein is not particularly limited as long as it can express the DNA of the present invention. Any known hosts such as *Escherichia coli*, yeast, insect cells, and animal cells can be used by matching with an expression vector system.

Examples thereof include bacteria belonging to the genus *Escherichia* such as *Escherichia coli*, those belonging to the genus *Bacillus* such as *Bacillus subtilis*, those belonging to the genus *Pseudomonas* such as *Pseudomonas putida*, those belonging to the genus *Rhizobium* such as *Rhizobium meliloti*, yeasts such as *Saccharomyces cervisiae, Schizosaccharomyces pombe*, and *Pichia pastoris*, other COS cells, animal cells such as CHO cells, and insect cells such as Sf19 and Sf21.

When a bacterium such as *Escherichia coli* is used as a host, it is preferable that it be possible for the recombinant vector of the present invention to be autonomously replicated in such bacterium and that the vector be composed of a promoter, a ribosome binding sequence, the gene of the present invention, and a transcription termination sequence. In addition, a gene capable of controlling a promoter may be contained therein. Examples of *Escherichia coli* include an *Escherichia coli* K12 strain and an *Escherichia coli* B strain. Examples of *Bacillus subtilis* include *Bacillus subtilis* MI 114 and 207-21. A promoter is not particularly limited as long as expression can be caused in a host such as *Escherichia coli* described above. Examples thereof include promoters derived from *Escherichia coli* and phages such as a trp promoter, a lac promoter, a $P_L$ promoter, and a $P_R$ promoter. In addition, artificially designed or modified promoter such as a tac promoter may also be used. A method for introducing a recombinant vector into a bacterium is not particularly limited. Examples thereof include the method using calcium ions (Cohen, S. N. et al.: Proc. Natl. Acad. Sci., USA, 69: 2110-2114 (1972)) and an electroporation method.

When yeasts are used as hosts, *Saccharomyces cervisiae, Schizosaccharomyces. pombe*, and *Pichia pastoris*, and the like can be used. A promoter is not particularly limited as long as expression can be caused in a yeast. Examples thereof include a gal1 promoter, a gal10 promoter, a heat-shock protein promoter, an MFα1 promoter, a PHO5 promoter, a PGK promoter, a GAP promoter, an ADH promoter, and an AOX1 promoter. A method for introducing a vector into a yeast is not particularly limited. Examples thereof include the electroporation method (Becker, D. M. et al.: Methods. Enzymol., 194: 182-187 (1991)), the spheroplast method (Hinnen, A. et al.: Proc. Natl. Acad. Sci., USA, 75: 1929-1933 (1978)), and the lithium acetate method (Itoh, H.: J. Bacteriol., 153: 163-168 (1983)).

Also, a cell-free protein synthesis system using a T7 promoter or the like for in vitro protein synthesis can be used. Examples of a cell-free protein synthesis system that can be used include a PURE SYSTEM (Post Genome Institute Co., Ltd.). Since cell culture is necessary for protein synthesis in a cell system, not only biohazard concerns arising from complex operations but also growth inhibition of culture cell lines caused by a synthetic protein are problematic. Meanwhile, a cell-free protein synthesis system is advantageous in the following regards: (1): any problematic factor related to the handling of viable cells (e.g., complications upon cell culture) can be resolved; (2): even proteins that are toxic to cells can be produced; (3): operations are relatively simplified and thus a protein of interest can be obtained in a short period of time, resulting in high-throughput synthesis; and (4): a non-natural amino acid can be readily introduced and thus a protein of interest can be labeled with ease.

5. Purification of a Synthesized Luciferase

When the dATP-induced activity of a synthesized mutant firefly luciferase is measured, it is necessary to purify the luciferase protein from the synthesis system used. In particular, in such case, it is necessary to completely remove components capable of serving as luciferase substrates such as ATP and the like contained in the relevant synthesis system. In order to remove such components and to recover a luciferase, known systems involving dialysis, ultrafiltration, a variety of column chromatography, and the like can be used.

When the amount of the synthesized luciferase is small (approximately 500 ng), a method comprising introducing a tag sequence into the luciferase protein and recovering the luciferase with the use of an affinity to the tag sequence is preferable. For instance, when a luciferase is synthesized in a cell-free protein synthesis system (PURE SYSTEM), the luciferase can be recovered with the introduction of a Strep-tag sequence (Trp-Ser-His-Pro-Gln-Phe-Glu-Lys: SEQ ID NO: 27), a Flag-tag sequence (Asp-Tyr-Lys-Asp-Asp-Asp-Asp-Lys: SEQ ID NO: 28), or the like as a tag sequence.

6. Measurement of the Activity of a Synthesized Luciferase (Activity Evaluation Method)

For measurement of the activity of a synthetic protein, a known luminometer capable of detecting luminescence can be used. However, an apparatus with an auto-reagent dispensing function is preferable.

Figure 2:
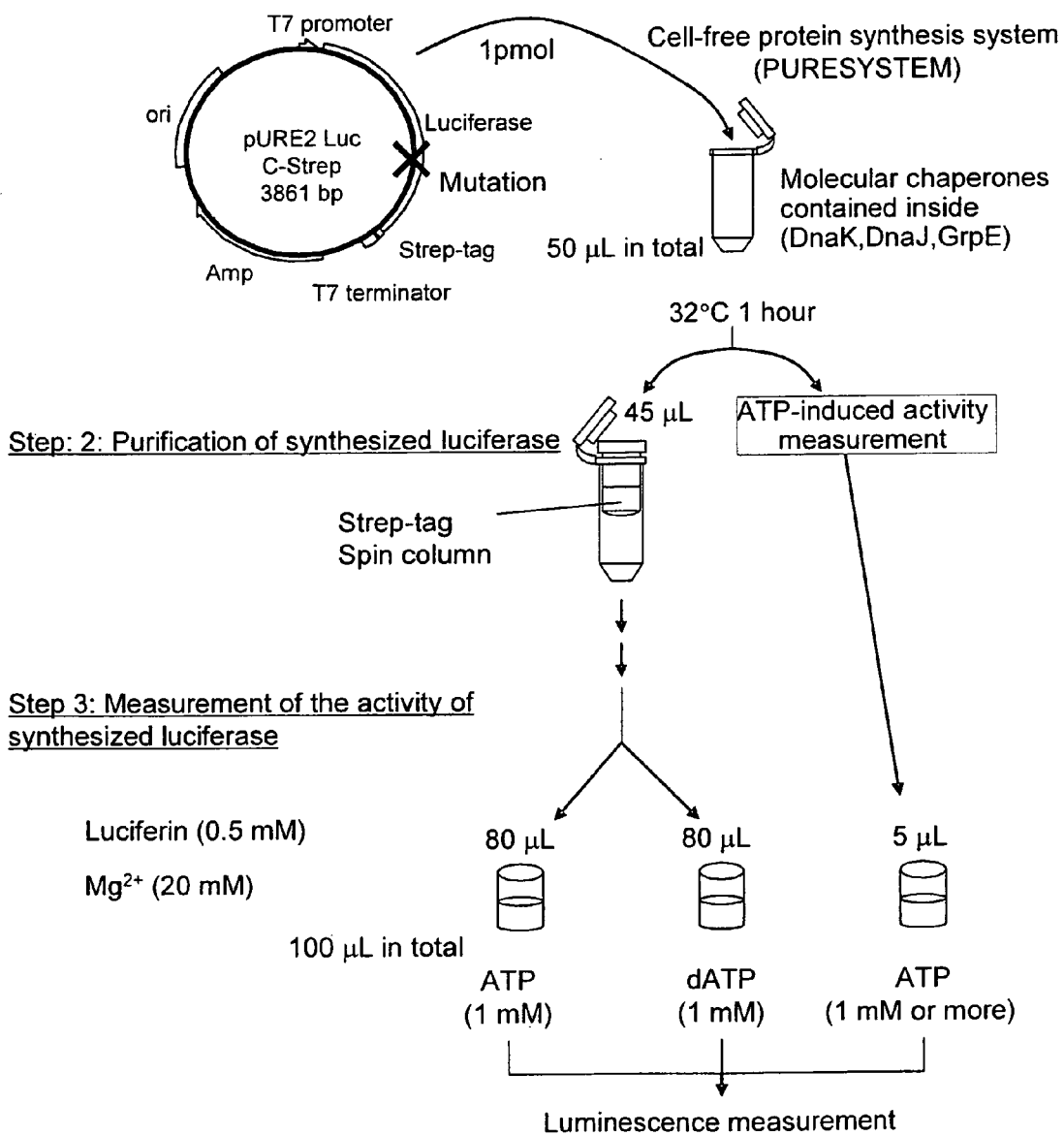
FIG. 2 is a flowchart showing the overall flow of measurement of the activity of the firefly luciferase of the present invention.

Overall Flow of Measurement of the Activity of a Mutant Firefly Luciferase:

The method for measuring the activity of a mutant firefly luciferase of the present invention is summarized in FIG. 2. The method mainly comprises 3 steps. In step 1, a mutant firefly luciferase is synthesized (preferably in a cell-free protein synthesis system). In step 2, the synthesized luciferase is purified using a Strep-tag column such that endogenous ATP contained in a synthesis reaction solution is completely removed. In step 3, the dATP-induced activity and the ATP-induced activity for a synthesized luciferase are measured. The above steps can be carried out in a consecutive manner and thus all steps can be carried out in approximately 2.5 hours. Thus, the method is very useful for evaluation of a luciferase with poor stability. The activity measurement method is described in the following Examples in greater detail.

EXAMPLES

The present invention is hereafter described in greater detail with reference to the following examples, although the technical scope of the present invention is not limited thereto.

Example 1

Production and Activity Measurement of a 422$^{nd}$-Amino-Acid Mutant Luciferase (1) Introduction of a Tag Sequence Into a Luciferase Gene The wild-type North American firefly luciferase gene was inserted into a pURE2 vector (Post Genome Institute Co., Ltd.) to prepare a pURE2 Luc vector and then a Strep-tag sequence was introduced into the C terminal of the luciferase gene contained in the pURE2 Luc vector.

An inverse PCR method was used for introduction. A pair of primers was designed in a manner such that the primers were positioned back-to-back with each other across a target site for tag sequence introduction (the C-terminal cite of luciferase) on the circular template DNA (pURE2Luc vector). In such case, a tag sequence to be introduced was added as an anchor sequence to the 5' terminal of each primer. PCR reaction was carried out under the above conditions such that linear double-strand DNA in which an anchor sequence had been added to the terminal was amplified. The obtained product was subjected to a self-ligation reaction for binding. Thus, a circular double-strand DNA in which an anchor sequence (tag sequence) had been introduced into a desired site was obtained.

Specifically, the primers used herein were as follows. All primers used herein were those synthesized by SIGMA GENOSYS.

```
                                          (SEQ ID NO: 1)
Luc-cStrep IF: 5'-TCGAAAAATAAAAGCTTTAGCATAACCCCT-3'
                                          (SEQ ID NO: 2)
Luc-cStrep IR: 5'-ACTGCGGGTGGCTCCACAATTTGGACTTTCCGC
                  CC-3'
```

The underlined parts each indicate a nucleotide sequence encoding a target Strep-tag sequence for introduction. In addition, in a case in which self-ligation reaction is carried out in a correct manner with the use of the above nucleotide sequence, the restriction enzyme BstBI sequence (TTCGAA) is newly formed.

The following components were added to a reaction solution for inverse PCR and the resultant was adjusted to a total volume of 50 μL: a template pURE2 Luc vector (20 fmol); a Luc-cStrep IF primer and a Luc-cStrep IR primer (15 pmol each); KOD-Plus Ver. 2 polymerase (2.5 U, TOYOBO); 10×KOD buffer (5 μL); 25 mM MgSO$_4$ (3 μL); and 2.0 mM dNTPs each (5 μL). An amplification reaction involving a reaction at 94° C. for 2 minutes, 40 cycles of 98° C. for 10 seconds, 60° C. for 30 seconds, and 68° C. for 4 minutes, and a reaction at 68° C. for 3 minutes was carried out.

A microchip electrophoresis apparatus (Hitachi Chemical Co., Ltd.) was used to confirm an amplification product obtained after the reaction. After confirmation of the absence of extra amplified DNA chains that were not the DNA of interest, DpnI (1 μL, 20 U/μL; NEB) was added to the rest of the sample (49 μL), followed by reaction at 37° C. for 1 hour for degradation of the plasmid of the template. Further, the reactant was purified using a QIAquick PCR Purification Kit (QIAGEN).

The purified reactant (5 μL) was mixed with T4 kinase (1 μL, TaKaRa) and a Ligation high solution (14 μL, TOYOBO), followed by reaction at 37° C. for 1 hour. A Ligation high solution (15 μL) was further added thereto, followed by reaction at 16° C. for 30 minutes for a self-ligation reaction.

The self-ligation reaction solution (5 μL) was mixed with competent cell MAX Efficiency DH5α (40 μL, Invitrogen) and a heat shock reaction was carried out at 42° C. for 40 seconds, followed by transformation into *Escherichia coli*. Further, the reaction solution was seeded on an LB-amp plate (LB BROTH BASE (Invitrogen), agar (Wako Pure Chemical Industries, Ltd.), and ampicilin (SIGMA)), followed by overnight incubation at 37° C. Thus, *Escherichia coli* colonies were formed. Several colonies were selected therefrom and cultured overnight in an LB-amp medium (1.5 mL).

Plasmids were purified from the cultured *Escherichia coli* with the use of a Plasmid Mini Kit (QIAGEN). Aliquots of the purified plasmids were treated with a BstBI restriction enzyme to conform that a DNA sequence encoding Strep-tag had been introduced therein. Further, the luciferase portion of each plasmid was subjected to full-length sequence analysis. Then, the occurrence or nonoccurrence of correct introduction of the Strep-tag DNA sequence and the presence or absence of PCR errors were confirmed.

(2) Production of Recombinant Vectors Each Comprising a Mutant Luciferase Gene

Site-specific substitution was induced in the DNA nucleotide sequence with the use of, as a template, a pURE2 Luc C-Strep vector comprising the wild-type North American firefly luciferase gene to which a Strep-tag sequence has been bound at the C terminal in a manner such that a gene encoding the $422^{nd}$ amino acid (Asp) was substituted with a gene encoding alanine (Ala), asparagine (Asn), or serine (Ser). For such substitution, a Gene Tailor Site-Directed Mutagenesis System (Invitrogen) was used in accordance with the manufacturer's protocols. The primers used for mutation were as follows. In addition, sequence analysis of each vector subjected to mutation was carried out in order to confirm the occurrence or nonoccurrence of mutation and the presence or absence of PCR errors.

```
                            (SEQ ID NO: 3)
Asp422-R:   5'-TCCAGAATGTAGCCATCCATCCTTGTCAATC
            A-3'
                            (SEQ ID NO: 4)
Asp422Ala-F: 5'-ATGGATGGCTACATTCTGGAgcgATAGCTTACTG
            G-3'
                            (SEQ ID NO: 5)
Asp422Asn-F: 5'-ATGGATGGCTACATTCTGGAaacATAGCTTACTG
            G-3'
                            (SEQ ID NO: 6)
Asp422Ser-F: 5'-ATGGATGGCTACATTCTGGAagcATAGCTTACTG
            G-3'
```

(3) Mutant Luciferase Synthesis in a Cell-Free Protein Synthesis System

Each vector was used as a temperate in a cell-free protein synthesis system (PURE SYSTEM, Post Genome Institute Co., Ltd.). A synthesis reaction was carried out at 32° C. for 1 hour with the use of each vector (1 pmol) as a template in accordance with the protocol. In addition, molecular chaperones DnaK, DnaJ, and GrpE (Post Genome Institute Co., Ltd.) were added during the synthesis reaction at final concentrations of 4, 2, and 2 µM, respectively. Western blotting was performed in order to confirm whether or not a luciferase synthesis reaction had been carried out in a correct manner.

(4) Measurement of the Activity of Synthesized Luciferase

The ATP-induced activity of each synthesized luciferase was measured. The apparatus used for measurement was a small-size gene analysis apparatus comprising a photodiode as a detection unit, which was developed in the inventors' laboratory.

The solution (5 µL) obtained as a result of the reaction using the PURE SYSTEM, a 10 mM ATP solution (0.5 µL), and a 2×C buffer solution (50 µL; 120 mM Tricine, 4 mM EDTA, and 40 mM Mg-acetate (pH 7.5)) were mixed together. The resultant was adjusted with DW to a total volume of 99 µL and dispensed into a reaction vessel of the small-size gene analysis apparatus. In addition, a 50 mM Luciferin solution (SIGMA) was introduced into a dispenser of the apparatus. An enzymatic reaction was initiated by dispensing the solution into the reaction vessel (1 µL per measurement). Then, the luminescence of each mutant luciferase was measured. Upon comparison of luciferase activities obtained by measurement, the maximum value of the luminescence intensity (V) obtained upon each measurement was used.

As a result, every luciferase for which Asp422 had been substituted with Ala, Asn, or Ser had a luminescence intensity of 0.01 (V) or less, which was equivalent to the detection noise level, indicating that the activity induced by ATP was lost. Thus, the $422^{nd}$ amino acid (Asp) was found to be an amino acid essential for luciferase activity.

Example 2

Production and Activity Measurement of a $421^{st}$-Amino-Acid Mutant Luciferase (1) Production of Recombinant Vectors Each Comprising a Mutant Luciferase Gene Site-specific substitution was induced in the DNA nucleotide sequence with the use of, as a template, a pURE2 Luc C-Strep vector comprising the wild-type North American firefly luciferase gene to which a Strep-tag sequence has been bound at the C terminal in a manner such that a gene encoding the $421^{st}$ amino acid (Gly) was substituted with a gene encoding any one of the other 19 different amino acids. For such substitution, a GeneTailor Site-Directed Mutagenesis System (Invitrogen) was used in accordance with the manufacturer's protocols. The primer sequences used for mutation were as follows. In addition, sequence analysis of each vector subjected to mutation was carried out in order to confirm the occurrence or nonoccurrence of mutation and the presence or absence of PCR errors.

```
                            (SEQ ID NO: 7)
Gly421-R:    5'-AGAATGTAGCCATCCATCCTTGTCAATCAAG
             G-3'
                            (SEQ ID NO: 8)
Gly421Ala-F: 5'-AGGATGGATGGCTACATTCTgcgGACATAGCTTA
             C-3'
                            (SEQ ID NO: 9)
Gly421Arg-F: 5'-AGGATGGATGGCTACATTCTcgcGACATAGCTTA
             C-3'
                            (SEQ ID NO: 10)
Gly421Asn-F: 5'-AGGATGGATGGCTACATTCTaacGACATAGCTTA
             C-3'
                            (SEQ ID NO: 11)
Gly421Asp-F: 5'-AGGATGGATGGCTACATTCTgatGACATAGCTTA
             C-3'
                            (SEQ ID NO: 12)
Gly421Cys-F: 5'-AGGATGGATGGCTACATTCTtgcGACATAGCTTA
             C-3'
                            (SEQ ID NO: 13)
Gly421Gln-F: 5'-AGGATGGATGGCTACATTCTcagGACATAGCTTA
             C-3'
                            (SEQ ID NO: 14)
Gly421Glu-F: 5'-AGGATGGATGGCTACATTCTgagGACATAGCTTA
             C-3'
                            (SEQ ID NO: 15)
Gly421His-F: 5'-AGGATGGATGGCTACATTCTcatGACATAGCTTA
             C-3'
                            (SEQ ID NO: 16)
Gly421Ile-F: 5'-AGGATGGATGGCTACATTCTattGACATAGCTTA
             C-3'
                            (SEQ ID NO: 17)
Gly421Leu-F: 5'-AGGATGGATGGCTACATTCTctgGACATAGCTTA
             C-3'
                            (SEQ ID NO: 18)
Gly421Lys-F: 5'-AGGATGGATGGCTACATTCTaaaGACATAGCTTA
             C-3'
                            (SEQ ID NO: 19)
Gly421Met-F: 5'-AGGATGGATGGCTACATTCTatgGACATAGCTTA
             C-3'
                            (SEQ ID NO: 20)
```

```
Gly421Phe-F:  5'-AGGATGGATGGCTACATTCTtttGACATAGCTTA
              C-3'

(SEQ ID NO: 21)
Gly421Pro-F:  5'-AGGATGGATGGCTACATTCTccgGACATAGCTTA
              C-3'

(SEQ ID NO: 22)
Gly421Ser-F:  5'-AGGATGGATGGCTACATTCTagcGACATAGCTTA
              C-3'

(SEQ ID NO: 23)
Gly421Thr-F:  5'-AGGATGGATGGCTACATTCTaccGACATAGCTTA
              C-3'

(SEQ ID NO: 24)
Gly421Trp-F:  5'-AGGATGGATGGCTACATTCTtggGACATAGCTTA
              C-3'

(SEQ ID NO: 25)
Gly421Tyr-F:  5'-AGGATGGATGGCTACATTCTtatGACATAGCTTA
              C-3'

(SEQ ID NO: 26)
Gly421Val-F:  5'-AGGATGGATGGCTACATTCTgtgGACATAGCTTA
              C-3'
```

(2) Mutant Luciferase Synthesis in a Cell-Free Protein Synthesis System

Each vector was used as a template in a cell-free protein synthesis system (PURE SYSTEM, Post Genome Institute Co., Ltd.). Synthesis reaction was carried out at 32° C. for 1 hour with the use of each vector as a template in accordance with the manufacturer's protocols. In addition, molecular chaperones DnaK, DnaJ, and GrpE (Post Genome Institute Co., Ltd.) were added during the synthesis reaction at final concentrations of 4, 2, and 2 μM, respectively. The ATP-induced activity in 5 μL of the solution subjected to the reaction was measured in the same manner as in Example 1.

(3) Purification of Synthesized Luciferases

Each luciferase comprising a Strep-tag sequence, which had been synthesized with the use of the PURE SYSTEM, was purified with the use of a Strep-tag affinity spin column. The spin column used was a Strep-Tactin Spin Column (IBA).

Firstly, Buffer W (500 μL; 100 mM Tris/HCl (pH 8), 150 mM NaCl, and 1 mM EDTA) provided with the Strep-Tactin Spin Column Kit was introduced into the spin column, followed by centrifugation at 1800 rpm for 30 seconds for washing of the column. Such operation was repeated once again. Next, in order to allow a luciferase to bind to the column, a solution containing a synthesized luciferase (approximately 45 μL) was added to the spin column, followed by centrifugation at 1800 rpm for 30 seconds. Further, in order to increase the amount of the binding luciferase, the filtrate was introduced again into the same spin column, followed by centrifugation in the same manner. After the filtrate was discarded, Buffer W (100 μL) was added to the spin column, followed by centrifugation at 13000 rpm for 30 seconds. Thus, unnecessary products adhering to the column were removed by washing. Such operation was repeated 3 times thereafter. The spin column was placed on a new tube. Then, in order to elute the luciferase binding to the column, Buffer BE (150 μL; 100 mM Tris-HCl (pH 8), 150 mM NaCl, 1 mM EDTA, and 2 mM D-biotin) provided with the Strep-Tactin Spin Column Kit was added thereto, followed by centrifugation at 1800 rpm for 30 seconds and at 13000 rpm for 15 seconds. The filtrate containing the eluted luciferase was recovered. Likewise, Buffer BE (50 μL) was added thereto and the operation was repeated once again. Thus, the filtrate (approximately 200 μL in total) was obtained.

(4) Measurement of the Activity of the Synthesized Luciferase

In order to measure the luciferase activity of the purified filtrate, a measurement solution was prepared. The filtrate (80 μL) was divided into two tubes, respectively. A 10×C buffer solution (10 μL; 600 mM Tricine, 20 mM EDTA, and 200 mM Mg-acetate (pH 7.5)) and 100 mM ATP (1 μL; final concentration: 1 mM) or 100 mM dATP (1 μL; final concentration: 1 mM) serving as a substrate were added to each tube. The resultant was adjusted with DW to a total volume of 99 μL and dispensed into a reaction vessel of a small-size gene analysis apparatus. In addition, a 50 mM Luciferin solution (SIGMA) was introduced into a dispenser of the apparatus. An enzymatic reaction was initiated by dispensing the solution into the reaction vessel (1 μL for a single measurement). Then, the luminescence of each mutant luciferase was measured. Upon comparison of luciferase activities obtained for each measurement, the maximum value of the luminescence intensity obtained upon each measurement was used.

Figure 3:
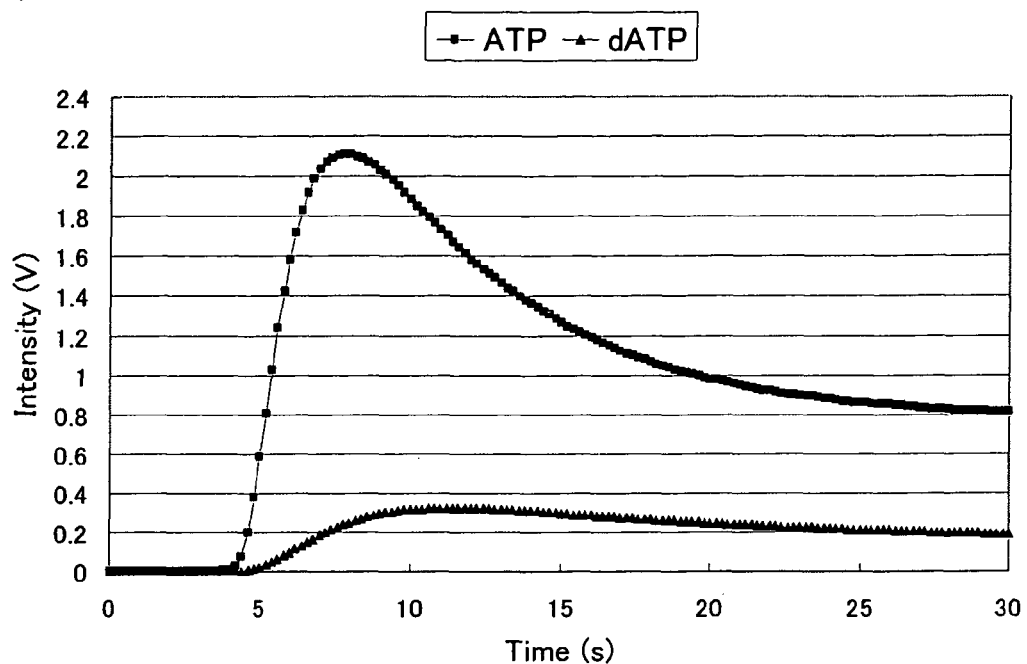
FIGS. 3(A) and 3(B) are graphs each showing the measurement results of the activity induced by ATP and the activity induced by dATP for a synthesized firefly luciferase ((A): the wild-type firefly luciferase; (B): the mutant firefly luciferase (Gly421Ser)).
Figure 3:
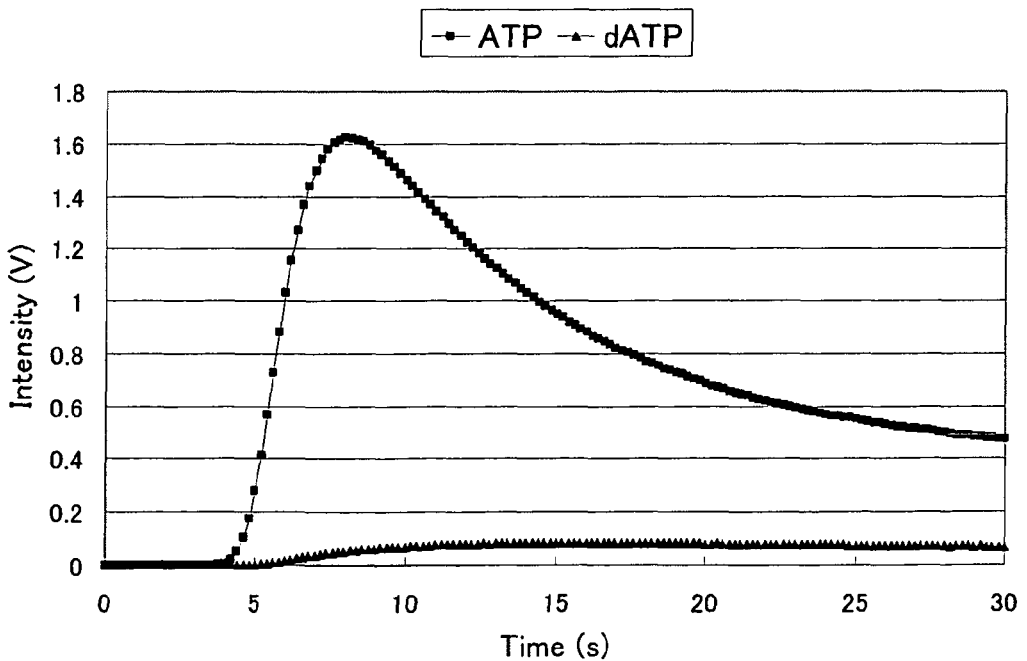

Each of FIGS. 3(A) and (B) is a graph showing the results obtained by synthesizing a luciferase, purifying the synthesized luciferase, and measuring the luminescence with the use of ATP and dATP as substrates. The horizontal axis represents reaction time (seconds) and the vertical axis represents luminescence intensity (V). FIG. 3(A) shows the measurement results for the wild-type North American firefly luciferase. FIG. 3(B) shows the measurement results for the mutant luciferase (Gly421Ser). In the case of the mutant luciferase (Gly421Ser), the dATP/ATP value (%) was found to be obviously lower than that in the case of the wild-type luciferase. All $421^{st}$-amino-acid mutants were subjected to the measurement.

The results indicating the activity of every mutant luciferase with a substitution of the $421^{st}$ amino acid are summarized in table 1. The values for Gly (No. 1) were obtained for the wild-type firefly luciferase.

TABLE 1

| No. | Amino acid | dATP/ATP (%) | ATP-induced activity | Category |
|---|---|---|---|---|
| 1 | Gly | 15.8 | 100.0 | |
| 2 | Ala | 14.3 | 54.7 | |
| 3 | Glu | 9.3 | 45.3 | |
| 4 | Met | 8.4 | 49.3 | |
| 5 | Gln | 8.2 | 58.7 | |
| 6 | Cys | 7.9 | 48.0 | |
| 7 | His | 7.3 | 50.7 | (a) |
| 8 | Tyr | 7.2 | 29.3 | |
| 9 | Lys | 7 | 61.3 | (a) |
| 10 | Asp | 5.9 | 56.0 | (a) |
| 11 | Ser | 5.1 | 65.3 | (a) |
| 12 | Phe | 5.1 | 21.3 | |
| 13 | Arg | 4.4 | 44.0 | (b) |
| 14 | Leu | 3.8 | 32.0 | |
| 15 | Asn | 3.6 | 38.7 | (b) |
| 16 | Thr | 2.6 | 13.3 | |
| 17 | Trp | N.D. | 24.0 | |
| 18 | Val | N.D. | 11.5 | |
| 19 | Ile | N.D. | 2.9 | |
| 20 | Pro | N.D. | 0.1> | |

The term "dATP/ATP (%)" used in table 1 refers to the proportion of dATP-induced activity to ATP-induced activity. Amino acids (No. 6 (Cys) to No. 10 (Asp)) are mutant amino acids each with a dATP/ATP value (%) equivalent to not less than ⅓ to ½ for that of the wild-type amino acid. Amino acids (No. 11 (Ser) to No. 16 (Thr)) are mutant amino acids each with a dATP/ATP value (%) equivalent to ⅓ or less for that of the wild-type amino acid. The results for No. 17 (Trp) to No. 20 (Pro) indicate that it was impossible to detect the dATP/ATP value.

The term "ATP-induced activity" used in table 1 refers to an ATP-induced activity value for a luciferase contained in a crude synthesis solution obtained as a result of luciferase synthesis. It is represented by a relative value when the level of the activity for the wild-type Gly421 is 100.

The term "category" used in table 1 includes both of the two groups described in "DESCRIPTION OF THE PREFERRED EMBODIMENTS." For the category (a) for which the maintenance of the activity induced by ATP is important, the most preferred example is Gly421Ser. For the category (b) for which the dATP/ATP percentage is important, the most preferred example is Gly421Asn.

INDUSTRIAL APPLICABILITY

With the use of the mutant firefly luciferase of the present invention, it becomes possible to use dATP as a DNA polymerase substrate upon pyrosequencing. Therefore, the present invention is useful in the fields of medicine, bio-life science, and the like, where nucleotide sequence analysis is necessary.

Free Text of Sequence Listing

```
SEQ ID NO: 1:    Primer (Luc-cStrep IF)
SEQ ID NO: 2:    Primer (Luc-cStrep IR)
SEQ ID NO: 3:    Primer (Asp422-R)
SEQ ID NO: 4:    Primer (Asp422Ala-F)
SEQ ID NO: 5:    Primer (Asp422Asn-F)
SEQ ID NO: 6:    Primer (Asp422Ser-F)
SEQ ID NO: 7:    Primer (Gly421-R)
SEQ ID NO: 8:    Primer (Gly421Ala-F)
SEQ ID NO: 9:    Primer (Gly421Arg-F)
SEQ ID NO: 10:   Primer (Gly421Asn-F)
SEQ ID NO: 11:   Primer (Gly421Asp-F)
SEQ ID NO: 12:   Primer (Gly421Cys-F)
SEQ ID NO: 13:   Primer (Gly421Gln-F)
SEQ ID NO: 14:   Primer (Gly421Glu-F)
SEQ ID NO: 15:   Primer (Gly421His-F)
SEQ ID NO: 16:   Primer (Gly421Ile-F)
SEQ ID NO: 17:   Primer (Gly421Leu-F)
SEQ ID NO: 18:   Primer (Gly421Lys-F)
SEQ ID NO: 19:   Primer (Gly421Met-F)
SEQ ID NO: 20:   Primer (Gly421Phe-F)
SEQ ID NO: 21:   Primer (Gly421Pro-F)
SEQ ID NO: 22:   Primer (Gly421Ser-F)
SEQ ID NO: 23:   Primer (Gly421Thr-F)
SEQ ID NO: 24:   Primer (Gly421Trp-F)
SEQ ID NO: 25:   Primer (Gly421Tyr-F)
SEQ ID NO: 26:   Primer (Gly421Val-F)
SEQ ID NO: 27:   Strep-tag sequence
SEQ ID NO: 28:   Flag-tag sequence
```

What is claimed is:

1. An isolated mutant firefly luciferase for which the proportion of activity induced by dATP to activity induced by ATP is lower than that for a wild-type North American firefly *Photinus pyralis* luciferase, which has an amino acid sequence in which the 421$^{st}$ amino acid glycine of the amino acid sequence of the wild-type North American firefly *Photinus pyralis* luciferase of SEQ ID NO:30 has been substituted with a polar amino acid selected from the group consisting of serine, lysine, aspartic acid, and histidine.

2. An isolated mutant firefly luciferase for which the proportion of activity induced by dATP to activity induced by ATP is lower than that for a wild-type North American firefly *Photinus pyralis* luciferase, which has an amino acid sequence in which the 421$^{st}$ amino acid glycine of the amino acid sequence of the wild-type North American firefly *Photinus pyralis* luciferase of SEQ ID NO: 30 has been substituted with a polar amino acid selected from the group consisting of arginine and asparagine.

3. The isolated mutant firefly luciferase according to claim 1, wherein the proportion of activity induced by dATP to activity induced by ATP is ½ or less of that for the wild-type luciferase and the ATP-induced activity is ½ or more of that for the wild-type luciferase.

4. The isolated mutant firefly luciferase according to claim 2, wherein the proportion of activity induced by dATP to activity induced by ATP is ⅓ or less of that for the wild-type luciferase and the ATP-induced activity is ⅓ to less than ½ of that for the wild-type luciferase.

5. A method for evaluating the activity of a mutant firefly luciferase, comprising the steps of:
synthesizing a mutant firefly luciferase for which the proportion of activity induced by dATP to activity induced by ATP (dATP/ATP) is lower than that for the wild-type North American firefly *Photinus pyralis* luciferase, which has an amino acid sequence in which the 421$^{st}$ amino acid glycine of the amino acid sequence of the wild-type North American firefly *Photinus pyralis* luciferase of SEQ ID NO:30 has been substituted with a polar amino acid selected from the group consisting of serine, lysine, aspartic acid, and histidine;
removing endogenous ATP from the synthesized mutant firefly luciferase and purifying the resultant; and
measuring the activity induced by ATP and the activity induced by dATP of the purified mutant firefly luciferase.

6. The method according to claim 5, wherein the mutant firefly luciferase is synthesized in a cell-free protein synthesis system.

7. A method for detecting a DNA or determining a DNA nucleotide sequence, wherein the mutant firefly luciferase according to claim 1 is used and at least dATP is used as a substrate.

8. A method for evaluating the activity of a mutant firefly luciferase, comprising the steps of:
synthesizing a mutant firefly luciferase for which the proportion of activity induced by dATP to activity induced by ATP (dATP/ATP) is lower than that for the wild-type North American firefly *Photinus pyralis* luciferase, which has an amino acid sequence in which the 421$^{st}$ amino acid glycine of the amino acid sequence of the wild-type North American firefly *Photinus pyralis* luciferase of SEQ ID NO: 30 has been substituted with a polar amino acid selected from the group consisting of arginine and asparagine;
removing endogenous ATP from the synthesized mutant firefly luciferase and purifying the resultant; and
measuring the activity induced by ATP and the activity induced by dATP of the purified mutant firefly luciferase.

9. The method according to claim 8, wherein the mutant firefly luciferase is synthesized in a cell-free protein synthesis system.

10. A method for detecting a DNA or determining a DNA nucleotide sequence, wherein the mutant firefly luciferase according to claim 2 is used and at least dATP is used as a substrate.

* * * * *

SEQUENCE LISTING

```
<160> NUMBER OF SEQ IDS NOS: 30

<210> SEQ ID NO 1
<211> LENGTH: 30
<212> TYPE: DNA
<213> ORGANISM: Artificial
<220> FEATURE:
<223> OTHER INFORMATION: Inventor: Tsunoda, Hiroyuki; Kanbara, Hideki
<220> FEATURE:
<223> OTHER INFORMATION: primer(Luc-cStrep IF)

<400> SEQUENCE: 1
tcgaaaaata aaagctttag cataacccct                                    30

<210> SEQ ID NO 2
<211> LENGTH: 35
<212> TYPE: DNA
<213> ORGANISM: Artificial
<220> FEATURE:
<223> OTHER INFORMATION: primer(Luc-cStrep IR)

<400> SEQUENCE: 2
actgcgggtg gctccacaat ttggactttc cgccc                              35

<210> SEQ ID NO 3
<211> LENGTH: 32
<212> TYPE: DNA
```

-continued

```
<213> ORGANISM: Artificial
<220> FEATURE:
<223> OTHER INFORMATION: primer(Asp422-R)

<400> SEQUENCE: 3
tccagaatgt agccatccat ccttgtcaat ca                                    32

<210> SEQ ID NO 4
<211> LENGTH: 35
<212> TYPE: DNA
<213> ORGANISM: Artificial
<220> FEATURE:
<223> OTHER INFORMATION: primer(Asp422Ala-F)

<400> SEQUENCE: 4
atggatggct acattctgga gcgatagctt actgg                                 35

<210> SEQ ID NO 5
<211> LENGTH: 35
<212> TYPE: DNA
<213> ORGANISM: Artificial
<220> FEATURE:
<223> OTHER INFORMATION: primer(Asp422Asn-F)

<400> SEQUENCE: 5
atggatggct acattctgga aacatagctt actgg                                 35

<210> SEQ ID NO 6
<211> LENGTH: 35
<212> TYPE: DNA
<213> ORGANISM: Artificial
<220> FEATURE:
<223> OTHER INFORMATION: primer(Asp422Ser-F)

<400> SEQUENCE: 6
atggatggct acattctgga agcatagctt actgg                                 35

<210> SEQ ID NO 7
<211> LENGTH: 32
<212> TYPE: DNA
<213> ORGANISM: Artificial
<220> FEATURE:
<223> OTHER INFORMATION: primer(Gly421-R)

<400> SEQUENCE: 7
agaatgtagc catccatcct tgtcaatcaa gg                                    32

<210> SEQ ID NO 8
<211> LENGTH: 35
<212> TYPE: DNA
<213> ORGANISM: Artificial
<220> FEATURE:
<223> OTHER INFORMATION: primer(Gly421Ala-F)

<400> SEQUENCE: 8
aggatggatg gctacattct gcggacatag cttac                                 35

<210> SEQ ID NO 9
<211> LENGTH: 35
<212> TYPE: DNA
<213> ORGANISM: Artificial
<220> FEATURE:
<223> OTHER INFORMATION: primer(Gly421Arg-F)

<400> SEQUENCE: 9
aggatggatg gctacattct cgcgacatag cttac                                 35
```

```
<210> SEQ ID NO 10
<211> LENGTH: 35
<212> TYPE: DNA
<213> ORGANISM: Artificial
<220> FEATURE:
<223> OTHER INFORMATION: primer(Gly421Asn-F)

<400> SEQUENCE: 10
aggatggatg gctacattct aacgacatag cttac                              35

<210> SEQ ID NO 11
<211> LENGTH: 35
<212> TYPE: DNA
<213> ORGANISM: Artificial
<220> FEATURE:
<223> OTHER INFORMATION: primer(Gly421Asp-F)

<400> SEQUENCE: 11
aggatggatg gctacattct gatgacatag cttac                              35

<210> SEQ ID NO 12
<211> LENGTH: 35
<212> TYPE: DNA
<213> ORGANISM: Artificial
<220> FEATURE:
<223> OTHER INFORMATION: primer(Gly421Cys-F)

<400> SEQUENCE: 12
aggatggatg gctacattct tgcgacatag cttac                              35

<210> SEQ ID NO 13
<211> LENGTH: 35
<212> TYPE: DNA
<213> ORGANISM: Artificial
<220> FEATURE:
<223> OTHER INFORMATION: primer(Gly421Gln-F)

<400> SEQUENCE: 13
aggatggatg gctacattct caggacatag cttac                              35

<210> SEQ ID NO 14
<211> LENGTH: 35
<212> TYPE: DNA
<213> ORGANISM: Artificial
<220> FEATURE:
<223> OTHER INFORMATION: primer(Gly421Glu-F)

<400> SEQUENCE: 14
aggatggatg gctacattct gaggacatag cttac                              35

<210> SEQ ID NO 15
<211> LENGTH: 35
<212> TYPE: DNA
<213> ORGANISM: Artificial
<220> FEATURE:
<223> OTHER INFORMATION: primer(Gly421His-F)

<400> SEQUENCE: 15
aggatggatg gctacattct catgacatag cttac                              35

<210> SEQ ID NO 16
<211> LENGTH: 35
<212> TYPE: DNA
<213> ORGANISM: Artificial
<220> FEATURE:
<223> OTHER INFORMATION: primer(Gly421Ile-F)
```

```
<400> SEQUENCE: 16
aggatggatg gctacattct attgacatag cttac            35

<210> SEQ ID NO 17
<211> LENGTH: 35
<212> TYPE: DNA
<213> ORGANISM: Artificial
<220> FEATURE:
<223> OTHER INFORMATION: primer(Gly421Leu-F)

<400> SEQUENCE: 17
aggatggatg gctacattct ctggacatag cttac            35

<210> SEQ ID NO 18
<211> LENGTH: 35
<212> TYPE: DNA
<213> ORGANISM: Artificial
<220> FEATURE:
<223> OTHER INFORMATION: primer(Gly421Lys-F)

<400> SEQUENCE: 18
aggatggatg gctacattct aaagacatag cttac            35

<210> SEQ ID NO 19
<211> LENGTH: 35
<212> TYPE: DNA
<213> ORGANISM: Artificial
<220> FEATURE:
<223> OTHER INFORMATION: primer(Gly421Met-F)

<400> SEQUENCE: 19
aggatggatg gctacattct atggacatag cttac            35

<210> SEQ ID NO 20
<211> LENGTH: 35
<212> TYPE: DNA
<213> ORGANISM: Artificial
<220> FEATURE:
<223> OTHER INFORMATION: primer(Gly421Phe-F)

<400> SEQUENCE: 20
aggatggatg gctacattct tttgacatag cttac            35

<210> SEQ ID NO 21
<211> LENGTH: 35
<212> TYPE: DNA
<213> ORGANISM: Artificial
<220> FEATURE:
<223> OTHER INFORMATION: primer(Gly421Pro-F)

<400> SEQUENCE: 21
aggatggatg gctacattct ccggacatag cttac            35

<210> SEQ ID NO 22
<211> LENGTH: 35
<212> TYPE: DNA
<213> ORGANISM: Artificial
<220> FEATURE:
<223> OTHER INFORMATION: primer(Gly421Ser-F)

<400> SEQUENCE: 22
aggatggatg gctacattct agcgacatag cttac            35

<210> SEQ ID NO 23
<211> LENGTH: 35
<212> TYPE: DNA
```

```
<213> ORGANISM: Artificial
<220> FEATURE:
<223> OTHER INFORMATION: primer(Gly421Thr-F)

<400> SEQUENCE: 23
aggatggatg gctacattct accgacatag cttac                              35

<210> SEQ ID NO 24
<211> LENGTH: 35
<212> TYPE: DNA
<213> ORGANISM: Artificial
<220> FEATURE:
<223> OTHER INFORMATION: primer(Gly421Trp-F)

<400> SEQUENCE: 24
aggatggatg gctacattct tgggacatag cttac                              35

<210> SEQ ID NO 25
<211> LENGTH: 35
<212> TYPE: DNA
<213> ORGANISM: Artificial
<220> FEATURE:
<223> OTHER INFORMATION: primer(Gly421Tyr-F)

<400> SEQUENCE: 25
aggatggatg gctacattct tatgacatag cttac                              35

<210> SEQ ID NO 26
<211> LENGTH: 35
<212> TYPE: DNA
<213> ORGANISM: Artificial
<220> FEATURE:
<223> OTHER INFORMATION: primer(Gly421Val-F)

<400> SEQUENCE: 26
aggatggatg gctacattct gtggacatag cttac                              35

<210> SEQ ID NO 27
<211> LENGTH: 8
<212> TYPE: PRT
<213> ORGANISM: Artificial
<220> FEATURE:
<223> OTHER INFORMATION: Strep-tag sequence

<400> SEQUENCE: 27

Trp Ser His Pro Gln Phe Glu Lys
1               5

<210> SEQ ID NO 28
<211> LENGTH: 8
<212> TYPE: PRT
<213> ORGANISM: Artificial
<220> FEATURE:
<223> OTHER INFORMATION: Flag-tag sequcne

<400> SEQUENCE: 28

Asp Tyr Lys Asp Asp Asp Asp Lys
1               5

<210> SEQ ID NO 29
<211> LENGTH: 1653
<212> TYPE: DNA
<213> ORGANISM: Photinus pyralis
<220> FEATURE:
<221> NAME/KEY: CDS
<222> LOCATION: (1)..(1653)
<223> OTHER INFORMATION:
```

<400> SEQUENCE: 29

```
atg gaa gac gcc aaa aac ata aag aaa ggc ccg gcg cca ttc tat cct        48
Met Glu Asp Ala Lys Asn Ile Lys Lys Gly Pro Ala Pro Phe Tyr Pro
1               5                   10                  15 cta gag gat gga acc gct gga gag caa ctg cat aag gct atg aag aga        96
Leu Glu Asp Gly Thr Ala Gly Glu Gln Leu His Lys Ala Met Lys Arg
            20                  25                  30 tac gcc ctg gtt cct gga aca att gct ttt aca gat gca cat atc gag       144
Tyr Ala Leu Val Pro Gly Thr Ile Ala Phe Thr Asp Ala His Ile Glu
        35                  40                  45 gtg aac atc acg tac gcg gaa tac ttc gaa atg tcc gtt cgg ttg gca       192
Val Asn Ile Thr Tyr Ala Glu Tyr Phe Glu Met Ser Val Arg Leu Ala
    50                  55                  60 gaa gct atg aaa cga tat ggg ctg aat aca aat cac aga atc gtc gta       240
Glu Ala Met Lys Arg Tyr Gly Leu Asn Thr Asn His Arg Ile Val Val
65                  70                  75                  80 tgc agt gaa aac tct ctt caa ttc ttt atg ccg gtt ttg ggc gcg tta       288
Cys Ser Glu Asn Ser Leu Gln Phe Phe Met Pro Val Leu Gly Ala Leu
                85                  90                  95 ttt atc gga gtt gca gtt gcg ccc gcg aac gac att tat aat gaa cgt       336
Phe Ile Gly Val Ala Val Ala Pro Ala Asn Asp Ile Tyr Asn Glu Arg
            100                 105                 110 gaa ttg ctc aac agt atg aac att tcg cag cct acc gta gtg ttt gtt       384
Glu Leu Leu Asn Ser Met Asn Ile Ser Gln Pro Thr Val Val Phe Val
        115                 120                 125 tcc aaa aag ggg ttg caa aaa att ttg aac gtg caa aaa aaa tta cca       432
Ser Lys Lys Gly Leu Gln Lys Ile Leu Asn Val Gln Lys Lys Leu Pro
    130                 135                 140 ata atc cag aaa att att atc atg gat tct aaa acg gat tac cag gga       480
Ile Ile Gln Lys Ile Ile Ile Met Asp Ser Lys Thr Asp Tyr Gln Gly
145                 150                 155                 160 ttt cag tcg atg tac acg ttc gtc aca tct cat cta cct ccc ggt ttt       528
Phe Gln Ser Met Tyr Thr Phe Val Thr Ser His Leu Pro Pro Gly Phe
                165                 170                 175 aat gaa tac gat ttt gta cca gag tcc ttt gat cgt gac aaa aca att       576
Asn Glu Tyr Asp Phe Val Pro Glu Ser Phe Asp Arg Asp Lys Thr Ile
            180                 185                 190 gca ctg ata atg aat tcc tct gga tct act ggg tta cct aag ggt gtg       624
Ala Leu Ile Met Asn Ser Ser Gly Ser Thr Gly Leu Pro Lys Gly Val
        195                 200                 205 gcc ctt ccg cat aga act gcc tgc gtc aga ttc tcg cat gcc aga gat       672
Ala Leu Pro His Arg Thr Ala Cys Val Arg Phe Ser His Ala Arg Asp
    210                 215                 220 cct att ttt ggc aat caa atc att ccg gat act gcg att tta agt gtt       720
Pro Ile Phe Gly Asn Gln Ile Ile Pro Asp Thr Ala Ile Leu Ser Val
225                 230                 235                 240 gtt cca ttc cat cac ggt ttt gga atg ttt act aca ctc gga tat ttg       768
Val Pro Phe His His Gly Phe Gly Met Phe Thr Thr Leu Gly Tyr Leu
                245                 250                 255 ata tgt gga ttt cga gtc gtc tta atg tat aga ttt gaa gaa gag ctg       816
Ile Cys Gly Phe Arg Val Val Leu Met Tyr Arg Phe Glu Glu Glu Leu
            260                 265                 270 ttt tta cga tcc ctt cag gat tac aaa att caa agt gcg ttg cta gta       864
Phe Leu Arg Ser Leu Gln Asp Tyr Lys Ile Gln Ser Ala Leu Leu Val
        275                 280                 285 cca acc cta ttt tca ttc ttc gcc aaa agc act ctg att gac aaa tac       912
Pro Thr Leu Phe Ser Phe Phe Ala Lys Ser Thr Leu Ile Asp Lys Tyr
    290                 295                 300 gat tta tct aat tta cac gaa att gct tct ggg ggc gca cct ctt tcg       960
Asp Leu Ser Asn Leu His Glu Ile Ala Ser Gly Gly Ala Pro Leu Ser
```

-continued

```
                    305                 310                 315                 320 aaa gaa gtc ggg gaa gcg gtt gca aaa cgc ttc cat ctt cca ggg ata         1008
Lys Glu Val Gly Glu Ala Val Ala Lys Arg Phe His Leu Pro Gly Ile
                        325                 330                 335 cga caa gga tat ggg ctc act gag act aca tca gct att ctg att aca         1056
Arg Gln Gly Tyr Gly Leu Thr Glu Thr Thr Ser Ala Ile Leu Ile Thr
            340                 345                 350 ccc gag ggg gat gat aaa ccg ggc gcg gtc ggt aaa gtt gtt cca ttt         1104
Pro Glu Gly Asp Asp Lys Pro Gly Ala Val Gly Lys Val Val Pro Phe
        355                 360                 365 ttt gaa gcg aag gtt gtg gat ctg gat acc ggg aaa acg ctg ggc gtt         1152
Phe Glu Ala Lys Val Val Asp Leu Asp Thr Gly Lys Thr Leu Gly Val
    370                 375                 380 aat cag aga ggc gaa tta tgt gtc aga gga cct atg att atg tcc ggt         1200
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga         1248
Tyr Val Asn Asn Pro Glu Ala Thr Asn Ala Leu Ile Asp Lys Asp Gly
                    405                 410                 415 tgg cta cat tct gga gac ata gct tac tgg gac gaa gac gaa cac ttc         1296
Trp Leu His Ser Gly Asp Ile Ala Tyr Trp Asp Glu Asp Glu His Phe
                420                 425                 430 ttc ata gtt gac cgc ttg aag tct tta att aaa tac aaa gga tat cag         1344
Phe Ile Val Asp Arg Leu Lys Ser Leu Ile Lys Tyr Lys Gly Tyr Gln
            435                 440                 445 gtg gcc ccc gct gaa ttg gaa tcg ata ttg tta caa cac ccc aac atc         1392
Val Ala Pro Ala Glu Leu Glu Ser Ile Leu Leu Gln His Pro Asn Ile
        450                 455                 460 ttc gac gcg ggc gtg gca ggt ctt ccc gac gat gac gcc ggt gaa ctt         1440
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa         1488
Pro Ala Ala Val Val Val Leu Glu His Gly Lys Thr Met Thr Glu Lys
                    485                 490                 495 gag atc gtg gat tac gtc gcc agt caa gta aca acc gcg aaa aag ttg         1536
Glu Ile Val Asp Tyr Val Ala Ser Gln Val Thr Thr Ala Lys Lys Leu
                500                 505                 510 cgc gga gga gtt gtg ttt gtg gac gaa gta ccg aaa ggt ctt acc gga         1584
Arg Gly Gly Val Val Phe Val Asp Glu Val Pro Lys Gly Leu Thr Gly
            515                 520                 525 aaa ctc gac gca aga aaa atc aga gag atc ctc ata aag gcc aag aag         1632
Lys Leu Asp Ala Arg Lys Ile Arg Glu Ile Leu Ile Lys Ala Lys Lys
        530                 535                 540 ggc gga aag tcc aaa ttg taa                                             1653
Gly Gly Lys Ser Lys Leu
545                 550

<210> SEQ ID NO 30
<211> LENGTH: 550
<212> TYPE: PRT
<213> ORGANISM: Photinus pyralis

<400> SEQUENCE: 30

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
```

-continued

```
             50                  55                  60
Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                     85                  90                  95

Phe Ile Gly Val Ala Val Ala Pro Ala Asn Asp Ile Tyr Asn Glu Arg
                100                 105                 110

Glu Leu Leu Asn Ser Met Asn Ile Ser Gln Pro Thr Val Val Phe Val
                115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
                290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
                370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
                450                 455                 460

Phe Asp Ala Gly Val Ala Gly Leu Pro Asp Asp Ala Gly Glu Leu
465                 470                 475                 480
```

-continued

```
Pro Ala Ala Val Val Val Leu Glu His Gly Lys Thr Met Thr Glu Lys
            485             490             495

Glu Ile Val Asp Tyr Val Ala Ser Gln Val Thr Thr Ala Lys Lys Leu
            500             505             510

Arg Gly Gly Val Val Phe Val Asp Glu Val Pro Lys Gly Leu Thr Gly
        515             520             525

Lys Leu Asp Ala Arg Lys Ile Arg Glu Ile Leu Ile Lys Ala Lys Lys
        530             535             540

Gly Gly Lys Ser Lys Leu
545             550
```